United States Patent
Jackson et al.

(10) Patent No.: US 6,844,289 B2
(45) Date of Patent: Jan. 18, 2005

(54) PROCESS FOR THE PREPARATION OF A NICKEL/PHOSPHOROUS LIGAND CATALYST

(75) Inventors: Scott Christopher Jackson, Wilmington, DE (US); Ronald J. McKinney, Wilmington, DE (US)

(73) Assignee: Invista North America S.A.R.L., Wilmington, DE (US)

( * ) Notice: Subject to any disclaimer, the term of this patent is extended or adjusted under 35 U.S.C. 154(b) by 118 days.

(21) Appl. No.: 10/409,482

(22) Filed: Apr. 8, 2003

(65) Prior Publication Data

US 2004/0204312 A1 Oct. 14, 2004

(51) Int. Cl.$^7$ .............................................. B01J 31/00
(52) U.S. Cl. ..................... 502/162; 502/169; 556/18; 556/138
(58) Field of Search ................ 502/162, 169; 556/18, 138

(56) References Cited

U.S. PATENT DOCUMENTS

| | | |
|---|---|---|
| 3,846,461 A | 11/1974 | Shook, Jr. |
| 3,903,120 A | 9/1975 | Shook, Jr. et al. |
| 5,512,695 A | 4/1996 | Kreutzer et al. |
| 5,512,696 A | 4/1996 | Kreutzer et al. |
| 5,523,453 A | 6/1996 | Breikss |
| 5,663,369 A | 9/1997 | Kreutzer et al. |
| 5,688,986 A | 11/1997 | Tam et al. |
| 5,693,843 A | 12/1997 | Breikss et al. |
| 5,723,641 A | 3/1998 | Tam et al. |
| 5,959,135 A | 9/1999 | Garner et al. |
| 6,069,267 A | 5/2000 | Tam |
| 6,120,700 A | 9/2000 | Foo et al. |
| 6,171,996 B1 | 1/2001 | Garner et al. |
| 6,171,997 B1 | 1/2001 | Foo et al. |
| 6,399,534 B2 * | 6/2002 | Bunel et al. ................. 502/155 |

\* cited by examiner

*Primary Examiner*—Mark L. Bell
*Assistant Examiner*—J. Pasterczyk

(57) ABSTRACT

Process for preparing a nickel/ligand catalyst in which a crude ligand mixture is contacted with at least one member selected from the group consisting of (i) a weakly acidic organic resin, (ii) a weakly basic organic resin, (iii) a high-surface-area organic resin, (iv) activated carbon, (v) aluminosilicate zeolite, (vi) a two phase solvent system for liquid-liquid extraction and (vii) a Lewis acid; recovering a solution containing a ligand of the formula $(R^1O)_2POZOP(OR^1)_2$; and contacting the solution with nickel chloride in the presence of a nitrile solvent and a reducing metal which is more electropositive than nickel to produce the nickel/ligand catalyst.

17 Claims, No Drawings

US 6,844,289 B2

PROCESS FOR THE PREPARATION OF A NICKEL/PHOSPHOROUS LIGAND CATALYST

FIELD OF THE INVENTION

This invention relates to a process for the preparation of a catalyst which is a complex of nickel and a bidentate phosphorous compound.

BACKGROUND OF THE INVENTION

It is well known in the art that complexes of nickel with phosphorus-containing ligands are useful as catalysts in hydrocyanation reactions. Such nickel complexes using monodentate phosphites are known to catalyze hydrocyanation of butadiene to produce a mixture of pentenenitriles. These catalysts are also useful in the subsequent hydrocyanation of pentenenitriles to produce adiponitrile, an important intermediate in the production of nylon. It is further known that bidentate phoshite and phosphinite ligands can be used to form nickel-based catalysts to perform such hydrocyanation reactions.

U.S. Pat. No. 3,903,120 discloses a process for preparing zerovalent nickel complexes by reacting elemental nickel with a monodentate phosphorous ligand of the formula $PZ_3$ where Z is an alkyl or alkoxy group, preferably an aryloxy group. The process uses finely divided elemental nickel and is preferably carried out in the presence of a nitrile solvent. The reaction is taught to be carried out in the presence of excess ligand.

U.S. Pat. No. 3,846,461 discloses a process for preparing zerovalent nickel complexes of triorganophosphites by reacting triorganophosphite compounds with nickel chloride in the presence of a finely divided reducing metal which is more electropositive than nickel, and in the presence of a promoter selected from the group consisting of $NH_3$, $NH_4X$, $Zn(NH_3)_2X_2$, and mixtures of $NH_4X$ and $ZnX_2$, where X is a halide. Reducing metals include Na, Li, Mg, Ca, Ba, Sr, Ti, V, Fe, Co, Cu, Zn, Cd, Al, Ga, In, Sn, Pb, and Th, with Zn being preferred.

U.S. Pat. No. 5,523,453 discloses a method of preparing nickel hydrocyanation catalysts containing bidentate phosphorous ligands. Zero-valent nickel compounds that contain ligands that can be displaced by the bidentate phosphorous ligand are a preferred source of nickel. Two such compounds are $Ni(COD)_2$, where COD is 1,5-cyclooctadiene, and $(oTTP)_2Ni(C_2H_4)$, where oTTP is $P(O\text{-ortho-}C_6H_4CH_3)_3$. Alternatively, divalent nickel compounds may be combined with reducing agents to produce a suitable nickel source. In the latter method of preparing catalyst, as the temperature of the catalyst preparation increases, the catalyst formation rate increases, but the amount of degradation product also increases.

U.S. Pat. No. 6,069,267 describes a method for preparing a crude bidentate phosphorus-containing ligand suitable for use in the catalyst preparation. The resulting product is, however, not pure ligand, but rather a crude ligand mixture that contains byproducts of the reaction which may affect the rate of formation of the nickel-containing catalyst. That process does not provide for isolation and purification of the bidentate ligand. The present inventors observed that, compared to the use of purified ligand, such crude ligand mixtures do inhibit catalyst preparation reactions wherein divalent nickel compounds are contacted with reducing agents to produce the nickel catalyst.

Accordingly, in order to avoid costly purification of the ligand, there is a need in the art for a process for nickel catalyst preparation that counteracts the inhibiting effects of the impurities contained in the crude ligand.

SUMMARY OF THE INVENTION

The present invention is a process for preparing a nickel/ligand catalyst, said process comprising:

(a) contacting one molar equivalent of $PCl_3$ with about two molar equivalents of $R^1$ OH, wherein $R^1$ is a substituted or unsubstituted aryl group, and at least two molar equivalents of an organic base at a temperature between about −25 deg C. and about 35 deg C., to produce a first reaction product comprising a di(aryloxy) phosphorous chloride of the formula $(R^1O)_2PCl$ and a salt formed from the organic base, said salt being substantially insoluble in the first reaction product;

(b) contacting the first reaction product at a temperature between about −25 deg C. and about 35 deg C. with about one half molar equivalent of HO—Z—OH, wherein Z is a substituted or unsubstituted aryl group different from $R^1$, to produce a second reaction product comprising a solids content, provided that if less than three molar equivalents of organic base are used in step (a), then sufficient organic base is used in step (b) to bring the total amount of organic base used in steps (a) and (b) combined to at least three molar equivalents of organic base relative to the $PCl_3$;

(c) separating the solids content from the second reaction product by filtration or extraction with water to produce a crude ligand mixture, said solids content comprising a salt formed from the organic base used in step (a) and optionally in step (b);

(d) contacting the crude ligand mixture with at least one member selected from the group consisting of (i) a weakly acidic organic resin, (ii) a weakly basic organic resin, (iii) a high-surface-area organic resin, (iv) activated carbon, (v) aluminosilicate zeolite, (vi) a two phase solvent system for liquid-liquid extraction and (vii) a Lewis acid;

(e) recovering from the product of step (d) a solution containing a ligand of the formula $(R^1O)_2POZOP(OR^1)_2$; and (f) contacting the solution of step (e) with nickel chloride in the presence of a nitrile solvent and a reducing metal which is more electropositive than nickel to produce the nickel/ligand catalyst.

DETAILED DESCRIPTION OF THE INVENTION

It has been discovered that in a process for preparing a nickel/ligand catalyst comprising reaction of nickel chloride in the presence of a crude bidentate phosphite ligand with a reducing metal more electropositive than nickel, that various treatments of crude ligand may overcome deleterious rate inhibiting effects of byproduct impurities which are present in the crude ligand.

U.S. Pat. No. 6,069,267 describes a method for preparing bidentate phosphite ligands suitable for the instant process. The resulting product is, however, not pure ligand, but rather a crude ligand mixture that contains byproducts of the reaction. When this crude ligand mixture is reacted with nickel chloride in the presence of a reducing metal that is more electropositive than nickel, the reaction is slow compared to that when purified ligand is utilized. Without wishing to be bound to any particular theory, the present inventors believe that the slow reaction rate may be attributable to one or more byproducts in the crude ligand mixture.

It has been discovered that if a crude ligand mixture produced by the method of U.S. Pat. No. 6,069,267 is treated in accordance with the present invention, the rate of catalyst formation is increased. Suitable treatment methods include contacting the crude ligand mixture with the one or more of the following:

(1) a weakly acidic organic resin including organic polymers with carboxylic acid functional groups, such as Amberlyst CG-50 (Rohm & Haas), (2) a weakly basic organic resin including organic polymers with alkylamine functional groups, such as Amberlyst® 21 (Rohm & Haas), (3) a high-surface-area neutral organic resin including polystyrene adsorbent, such as Amberlite® XAD-4, and polyacrylate adsorbent, such as Amberlite® XAD-7 (Rohm & Haas), (4) activated carbon, (5) an aluminosilicate zeolite, commonly referred to in the art as molecular sieves, such as 3A or 13X molecular sieves, (6) a two phase solvent system for liquid-liquid extraction where one phase is a non-polar aliphatic hydrocarbon such as hexane or cyclohexane and the other phase is a polar organic species such as adiponitrile, methylglutaronitrile, ethylsuccinonitrile, acetonitrile, ethyleneglycol or propyleneglycol, and (7) a Lewis acid.

A solvent may be employed during the treatment to improve flowability and contact between the crude ligand and the treating agent. Suitable solvents include aliphatic hydrocarbons and nitrites. 3-Pentenenitrile is a preferred solvent.

The material used for treatment is then separated from the crude ligand mixture to recover a treated ligand mixture that is then reacted with nickel chloride in the presence of a nitrile solvent and a reducing metal, to form a nickel/ligand catalyst at a higher reaction rate than that obtained by using a untreated crude ligand mixture. The reducing metal, hereafter referred to as MET, can be any metal which is more electropositive than nickel. Such metals include Na, Li, K, Mg, Ca, Ba, Sr, Ti, V, Fe, Co, Cu, Zn, Cd, Al, Ga, In, Sn, Pb, and Th. Most preferred are Fe and Zn.

The source of nickel for this invention is preferably nickel (II) chloride, $NiCl_2$. Either hydrated or anhydrous forms of $NiCl_2$ may be used. Anhydrous $NiCl_2$ is preferred in order to minimize the hydrolytic degradation of the ligand. The expression "anhydrous" means that the nickel chloride contains less than 2% by weight water. Nickel chloride containing 1% or less water is preferred. Processes for producing anhydrous nickel chloride have been described in co-pending application Ser. No. 09/994,102. The expression "hydrated $NiCl_2$" means $NiCl_2$ containing 2% or more water by weight. Examples of hydrated $NiCl_2$ include the dihydrate, the hexahydrate and aqueous solutions of $NiCl_2$. Preferred sources for producing anhydrous $NiCl_2$ are the hexahydrate product and an aqueous solution. $NiCl_2$ as an aqueous solution is particularly preferred. The aqueous solution is available commercially as an approximately 29 weight percent $NiCl_2$ aqueous solution.

The catalyst formation reaction is carried out in the presence of a nitrile solvent, preferably 3-pentenenitrile or 2-methyl-butenenitrile. The concentration of ligand may range from about 1% to 90% by weight. For practical reasons the preferred range of ligand concentration is 5% to 50%. The amount of reducing metal (MET) will generally fall in the range of 0.1% to 5% of the reaction mass. The molar ratio of $NiCl_2$ to MET ranges from 0.1:1 to 100:1. The preferred ratio of $NiCl_2$:MET ranges from 2:1 to 50:1. The reaction temperature may range from 0° C. to 120° C. The preferred temperature range is dependent on the $NiCl_2$ form. Hydrated forms of $NiCl_2$ react rapidly at lower temperatures than anhydrous $NiCl_2$. For $NiCl_2.2H_2O$, the preferred temperature range is 0° C. to 60° C., and the most preferred range is 25° C. to 50° C. For anhydrous $NiCl_2$, the preferred temperature range is 30° C. to 110° C., and the most preferred range is 50° C. to 100° C. The reaction may be run within a wide pressure range. For practical reasons, the preferred pressure ranges from about 5 psia to 50 psia (34 to 340 kPa). The reaction may be run in batch or continuous mode.

Suitable ligands for the present invention are bidentate phosphorous-containing ligands selected from the group consisting of bidentate phosphites and bidentate phosphinites. Preferred ligands are bidentate phosphite ligands.

The preferred bidentate phosphite ligands are of the following structural formulae:

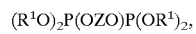

$(R^1O)_2P(OZO)P(OR^1)_2,$  I wherein $R^1$ is phenyl, unsubstituted or substituted with one or more $C_1$ to $C_{12}$ alkyl or $C_1$ to $C_{12}$ alkoxy groups; or naphthyl, unsubstituted or substituted with one or more $C_1$ to $C_{12}$ alkyl or $C_1$ to $C_{12}$ alkoxy groups; and Z is independently selected from the group consisting of structural formulae II, III, IV, V, and VI:

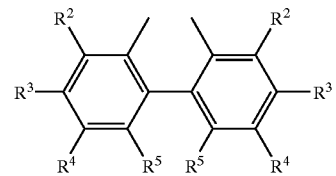

II

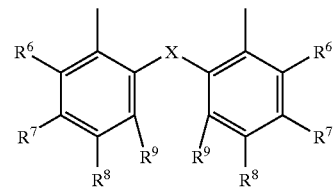

III wherein $R^2$, $R^3$, $R^4$, $R^5$, $R^6$, $R^7$, $R^8$, and $R^9$ are independently selected from the group consisting of H, $C_1$ to $C_{12}$ alkyl, and $C_1$ to $C_{12}$ alkoxy;

X is O, S, or CH($R^{10}$);

$R^{10}$ is H or $C_1$ to $C_{12}$ alkyl;

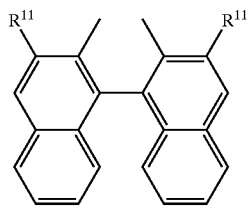

IV

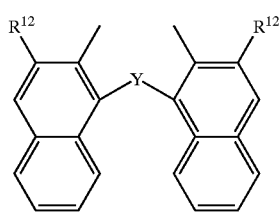

V wherein $R^{11}$ and $R^{12}$ are independently selected from the group consisting of H, $C_1$ to $C_{12}$ alkyl, and $C_1$ to $C_{12}$ alkoxy; and $CO_2R^{13}$, $R^{13}$ is $C_1$ to $C_{12}$ alkyl or $C_6$ to $C_{10}$ aryl, unsubstituted or substituted, with $C_1$ to $C_4$ alkyl;

Y is O, S, or CH($R^{14}$);

$R^{14}$ is H or $C_1$ to $C_{12}$ alkyl;

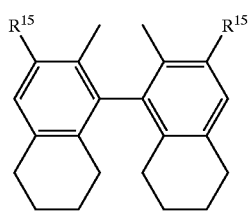

VI wherein $R^{15}$ is selected from the group consisting of H, $C_1$ to $C_{12}$ alkyl, and $C_1$ to $C_{12}$ alkoxy and $CO_2R^{16}$;

$R^{16}$ is $C_1$ to $C_{12}$ alkyl or $C_6$ to $C_{10}$ aryl, unsubstituted or substituted with $C_1$ to $C_4$ alkyl.

In the structural formulae I through VIII, the $C_1$ to $C_{12}$ alkyl, and $C_1$ to $C_{12}$ alkoxy groups may be straight chains or branched.

Examples of bidentate phosphite ligands that are useful in the present process include those having the formulae VII to XXIV, shown below wherein for each formula, $R^{17}$ is selected from the group consisting of methyl, ethyl or isopropyl, and $R^{18}$ and $R^{19}$ are independently selected from H or methyl:

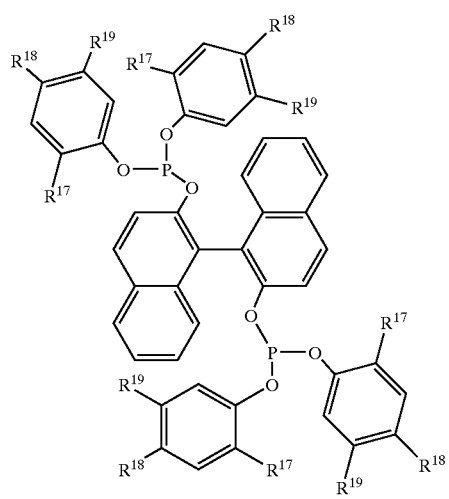

VII

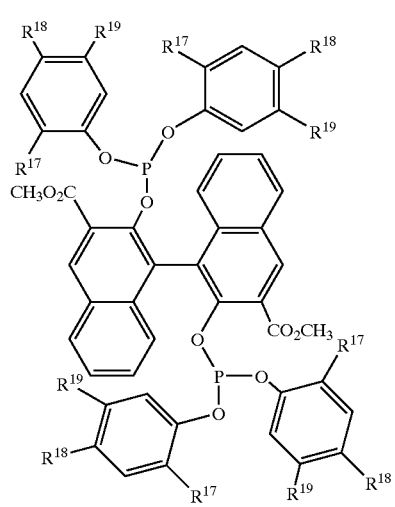

VIII

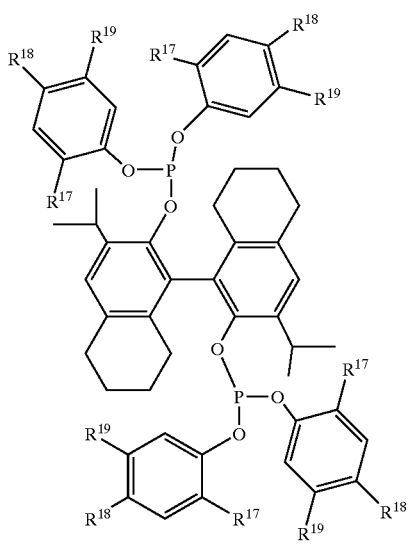

IX

X
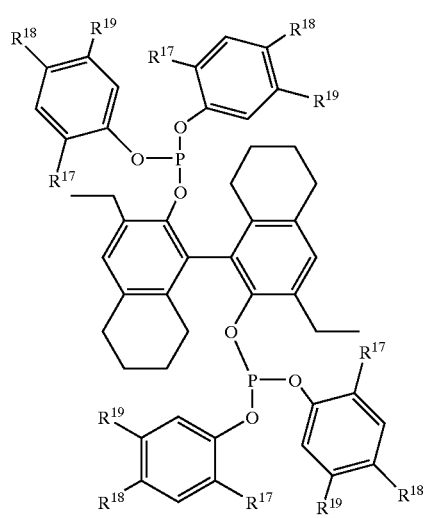
XI
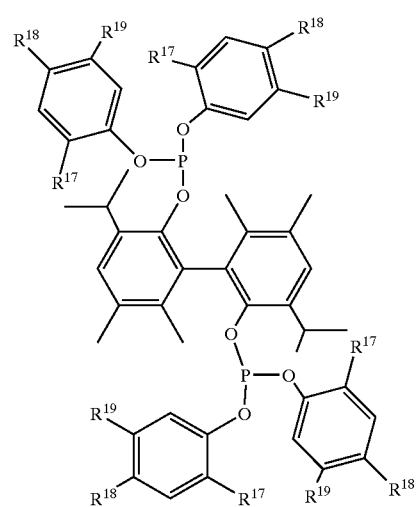
XII
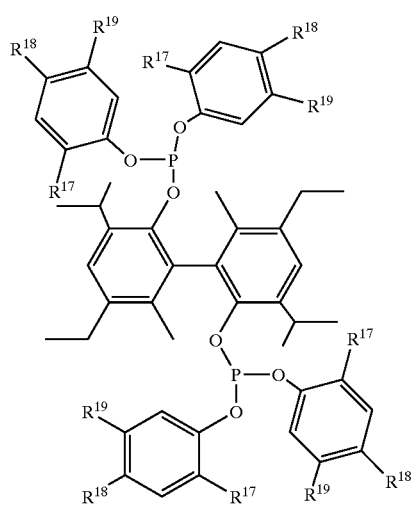
XII
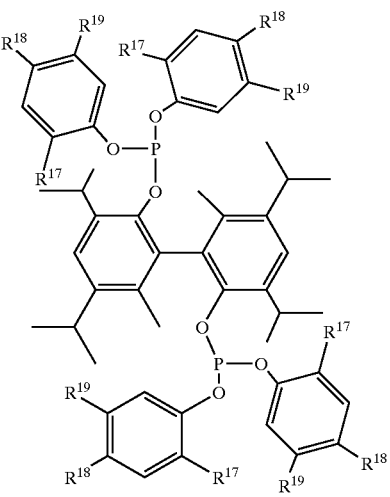
XIV
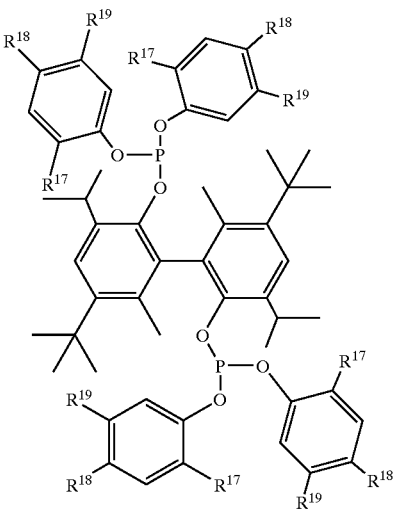
XV
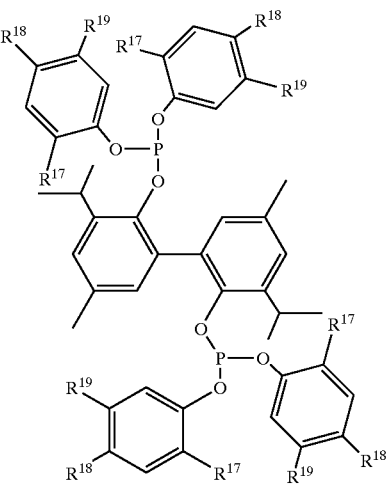

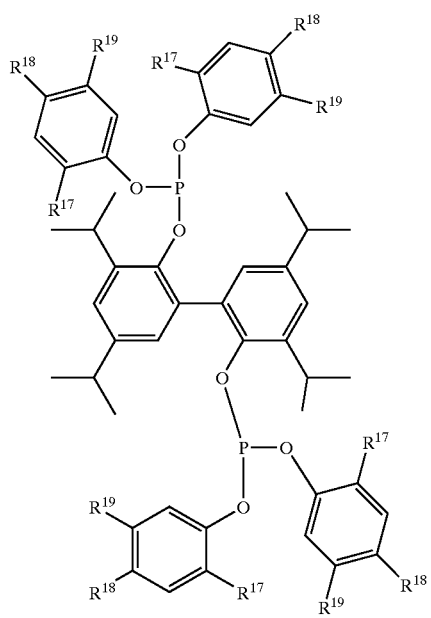
XVI
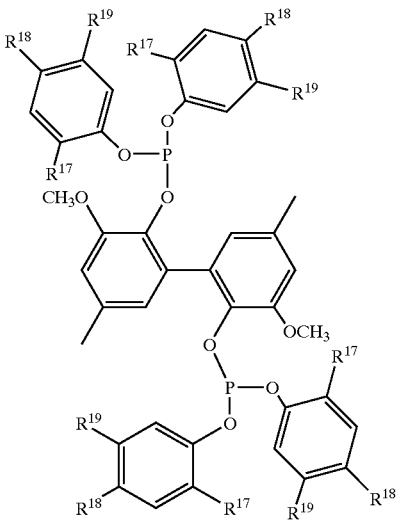
XIX
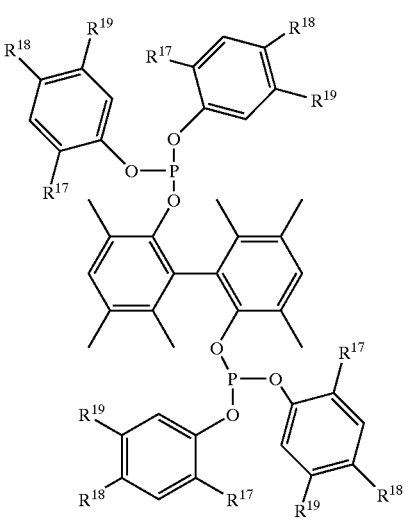
XX
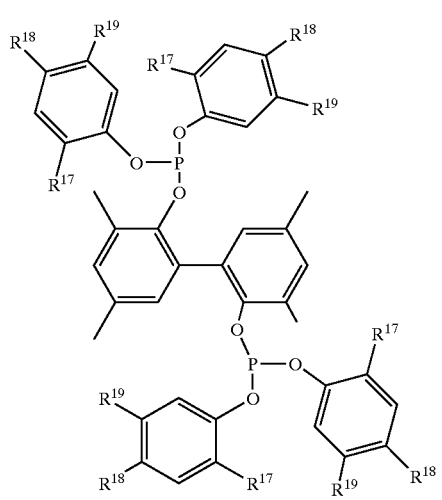
XVII
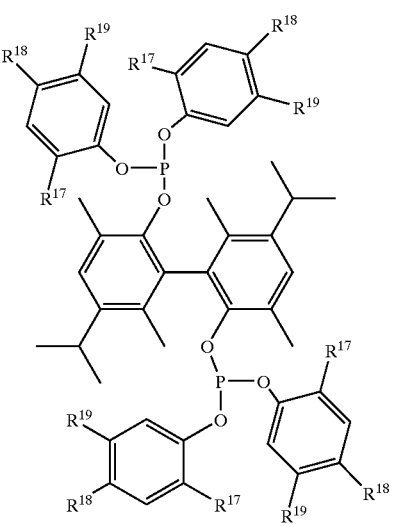
XXI
XVIII

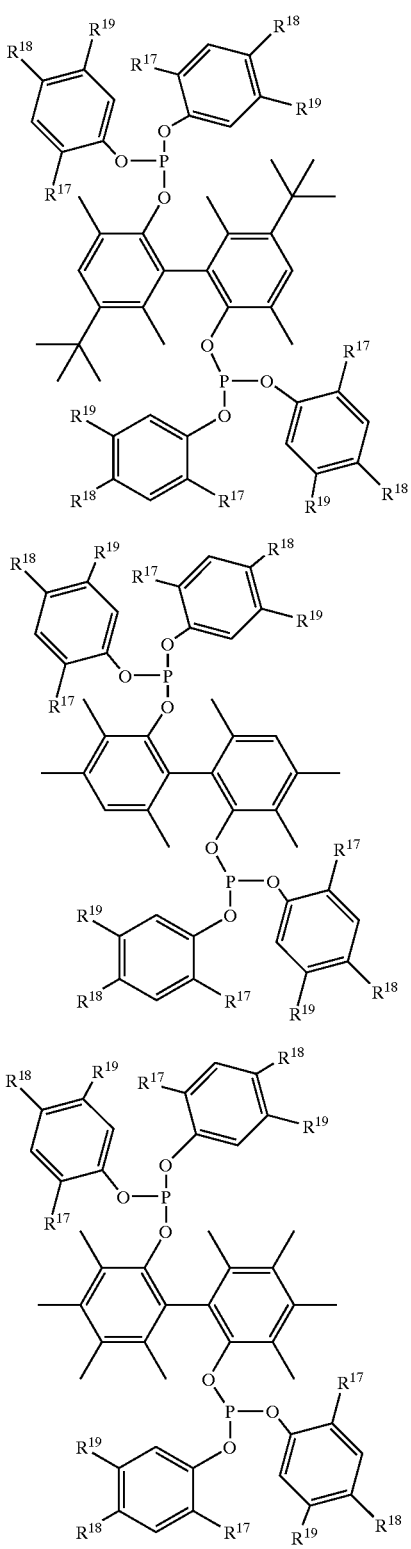

Additional suitable bidentate phosphites are of the type disclosed in U.S. Pat. Nos. 5,512,695; 5,512,696; 5,663,369; 5,688,986; 5,723,641; 5,847,101; 5,959,135; 6,120,700; 6,171,996; 6,171,997 and 6,399,534; the disclosures of which are incorporated herein by reference. Suitable bidentate phosphinites are of the type disclosed in U.S. Pat. Nos. 5,523,453 and 5,693,843, the disclosures of which are incorporated herein by reference.

The reaction may be carried out in a manner such that unreacted NiCl$_2$ and MET may be separated from the reaction product by filtration or centrifugation. The collected excess nickel chloride can then be recycled back to a catalyst preparation reactor.

EXAMPLES

The invention is illustrated by the following non-limiting examples. In the following examples, the reducing metal is the limiting reagent in each reaction, and therefore the extent of reaction (conversion) is expressed as the percentage of the reducing metal reacted. The extent of reaction (conversion) is determined by analyzing for the amount of active nickel produced by the catalyst synthesis reaction. The analysis is carried out by treating a solids-free aliquot of the reaction solution with dimethyl acetylenedicarboxylate (DMAD), which forms a stable nickel complex, (Ligand)Ni(DMAD), and analyzing quantitatively for this complex by High Pressure Liquid Chromatography (HPLC).

The Comparative Example illustrates typical reaction behavior when the crude ligand mixture is not treated according to this invention.

Examples 2, 3, and 5 illustrate that treating the crude ligand with various resins results in higher rates of reaction compared with reaction using no treatment of the ligand (Comparative Example). Example 6 illustrates the effect of treating the crude ligand with activated carbon. Examples 4 and 7 illustrate the positive effect of treatment with alumino silicate zeolites (molecular sieves). Examples 1, 8, and 10 illustrate the benefits of utilizing liquid-liquid extraction to treat the crude ligand mixture. Example 9 illustrates the benefits of treating the crude ligand mixture with small amount of a Lewis acid prior to the catalyst preparation.

For the Comparative Example and Examples 1 through 10, a "crude ligand VII" was prepared by
  a) treating a toluene solution of PCl$_3$ with two molar equivalents of thymol and three molar equivalents of triethylamine while maintaining a reaction temperature of about –5° C., to produce a first reaction product comprising di(2-isopropyl-5-methylphenoxy) phosphorus chloride, triethylammonium chloride (which is substantially insoluble in the mixture), unreacted triethylamine and toluene,
  b) adding one half molar equivalent of binaphthol (relative to PCl$_3$) to the reaction mixture while maintaining the reaction temperature at about –5° C.,
  c) treating the product of step (b) with water to extract the triethylammonium hydrochloride and separating the resulting aqueous lower phase from the organic product solution, and subsequently distilling a portion of the toluene from the organic product solution to produce a mixture comprising about 33 wt % ligand VII (werein R$^{17}$ is isopropyl, R$^{18}$ is H, and R$^{19}$ is methyl) in toluene, said mixture hereinafter referred to as "crude ligand VII".

"Ligand VII Stock Solution" was prepared by:
  (1) dissolving 830 grams of "crude ligand VII" in 1000 grams of 3-pentenenitrile in an air-free 3 liter round bottom flask fitted with an over head stirrer, a heating mantel, a distillation head, a dip tube to draw off material out of the flask and an addition funnel,
  (2) heating the solution from step (1) under vacuum to 45 to 60 deg C. to distill off the toluene and then allowing the solution to cool to ambient temperature.

Analysis showed this "Ligand VII Stock Solution" to have about 24 wt % ligand in it.

Comparative Example

"Ligand VII Stock Solution" (12.067 grams) was put into a dried 20 cc vial. Into this vial was also placed 0.493 grams of anhydrous $NiCl_2$ and 0.096 grams of finely divided zinc metal. A small magnetic stirring bar was added to the vial. The vial was capped and placed into a heated aluminum block that had been pre-heated to 100 deg C. A stop watch was started when the vial was placed into the heated block. The contents of the vial were agitated using a rotating magnetic bar coupled to the magnetic bar inside the vial. At 1.5 hours a sample was taken of the solution. Analysis of this sample showed 425 ppm of Ni as catalyst in solution.

Example 1

This example shows the benefit of extracting crude ligand with adiponitrile.

"Crude ligand VII" (830 grams) was combined with 1000 grams of adiponitrile in an air tight 3-liter round bottom flask. This flask was outfitted with an over head stirrer, a heating mantel, a distillation head, a dip tube to draw off material out of the flask and an addition funnel. This material was heated under vacuum to 45° to 60° C. to distill off the toluene. This mixture was allowed to cool, and about 1000 grams of cyclohexane was added to the flask. Two liquid phases formed. This solution was agitated and allowed to settle. The adiponitrile formed a heavy liquid phase which was drawn off as waste. About 1000 grams of 3-pentenenitrile was added to the flask. The flask was heated again under vacuum to about 45 deg C., and the cyclohexane was stripped off. The resulting solution was allowed to cool. A sample showed this final extracted ligand solution to have about 20 wt % ligand in it.

12.048 grams of this extracted ligand solution was put into a dried 20 cc vial. Into this vial was also placed 0.494 grams of anhydrous $NiCl_2$ and 0.094 grams of finely divided zinc metal. A small magnetic stirring bar was added to the vial. The vial was capped and placed into a heated aluminum block that had been pre-heated to 100 deg C. A stop watch was started when the vial was placed into the heated block. The contents of the vial were agitated using a rotating magnetic bar coupled to the magnetic bar inside the vial. At 1.5 hours a sample was taken of the solution. Analysis of this sample showed 5340 ppm of Ni as catalyst in solution. This is about 13 times the amount of catalyst made in the Comparative Example.

Example 2

This example shows the benefit of treating crude ligand with Amberlyst® 21 base resin (Rohm & Haas), a weakly basic resin containing alkylamine groups.

20 cc of Amberlyst® 21 base resin was loaded into a 50 cc syringe body. 50 cc of 3-pentenenitrile was flushed through the resin and was disposed of. About 15 grams of "Ligand VII Stock Solution" was then allowed to drain through the resin bed. The ligand solution was re-analyzed and found to have about 12 wt % ligand in it.

12.037 grams of this Amberlyst® resin treated ligand solution was put into a dried 20 cc vial. Into this vial was also placed 0.498 grams of anhydrous $NiCl_2$ and 0.098 grams of finely divided zinc metal. A small magnetic stirring bar was added to the vial. The vial was capped and placed into a heated aluminum block that had been pre-heated to 100 deg C. A stop watch was started when the vial was placed into the heated block. The contents of the vial were agitated using a rotating magnetic bar coupled to the magnetic bar inside the vial. At 1.5 hours a sample was taken of the solution. Analysis of this sample showed 2210 ppm of Ni as catalyst in solution. This is about 5 times the amount of catalyst made in the Comparative Example.

Example 3

This example shows the benefit of treating crude ligand with Amberlite® CG-50 (Rohm & Haas), a weakly acidic resin containing carboxylic acid groups.

20 cc of Amberlite® CG-50 acid resin (Rohm & Haas) was loaded into a 50 cc syringe body. 50 cc of 3-pentenenitrile was flushed through the resin and was disposed of. About 15 grams of "Ligand VII Stock Solution" was then allowed to drain through the resin bed. The ligand solution was re-analyzed and found to have about 15 wt % ligand in it.

12.045 grams of this Amberlite® CG-50 resin treated ligand solution was put into a dried 20 cc vial. Into this vial was also placed 0.494 grams of anhydrous $NiCl_2$ and 0.098 grams of finely divided zinc metal. A small magnetic stirring bar was added to the vial. The vial was capped and placed into a heated aluminum block that had been pre-heated to 100 deg C. A stop watch was started when the vial was placed into the heated block. The contents of the vial were agitated using a rotating magnetic bar coupled to the magnetic bar inside the vial. At 1.5 hours a sample was taken of the solution. Analysis of this sample showed 4230 ppm of Ni as catalyst in solution. This is nearly 10 times the amount of catalyst made in the Comparative Example.

Example 4

This example shows the benefit of treating crude ligand with small pore zeolites.

5 cc of 3A Molecular Sieves (zeolite), which had been previously activated by drying overnight at 350 deg C. was loaded into a 50 cc syringe body. 20 cc of 3-pentenenitrile was flushed through the resin and was disposed of. About 15 grams of "Ligand VII Stock Solution" was then allowed to drain through the sieves. The ligand solution was re-analyzed and found to have about 22 wt % ligand in it.

12.012 grams of this 3A molecular sieve treated ligand solution was put into a dried 20 cc vial. Into this vial was also placed 0.490 grams of anhydrous $NiCl_2$ and 0.092 grams of finely divided zinc metal. A small magnetic stirring bar was added to the vial. The vial was capped and placed into a heated aluminum block that had been pre-heated to 100 deg C. A stop watch was started when the vial was placed into the heated block. The contents of the vial were agitated using a rotating magnetic bar coupled to the magnetic bar inside the vial. At 1.5 hours a sample was taken of the solution. Analysis of this sample showed 2290 ppm of Ni as catalyst in solution. This is nearly 5 times the amount of catalyst made in the Comparative Example.

Example 5

This example shows the benefit of treating crude ligand with an adsorbent high-surface-area neutral organic resin.

5 cc of Amberlite® XAD-4 resin (Rohm & Haas), which had been previously washed with di-ionized water and vacuum dried overnight at 40 deg C., was loaded into a 50 cc syringe body. 20 cc of 3-pentenenitrile was flushed through the resin and was disposed of. About 15 grams of "Ligand VII Stock Solution" was then allowed to drain through the resin. The ligand solution was re-analyzed and found to have about 22 wt % ligand in it.

12.081 grams of this Amberlite® XAD-4 resin treated ligand solution were put into a dried 20 cc vial. Into this vial was also placed 0.495 grams of anhydrous $NiCl_2$ and 0.098 grams of finely divided zinc metal. A small magnetic stirring bar was added to the vial. The vial was capped and placed into a heated aluminum block that had been pre-heated to 100 deg C. A stop watch was started when the vial was placed into the heated block. The contents of the vial were agitated using a rotating magnetic bar coupled to the magnetic bar inside the vial. At 1.5 hours a sample was taken of the solution. Analysis of this sample showed 1360 ppm of Ni as catalyst in solution. This is about 3 times the amount of catalyst made in the Comparative Example.

Example 6

This example shows the benefit of treating crude ligand with activated carbon.

5 cc of DARCO® activated carbon, which had been previously washed with de-ionized water and vacuum dried overnight at 40 deg C., was loaded into a 50 cc syringe body. 20 cc of 3-pentenenitrile was flushed through the carbon bed and was disposed of. About 15 grams of Ligand VII Stock Solution was then allowed to drain through the carbon bed. The ligand solution was re-analyzed and found to have about 18 wt % ligand in it.

12.055 grams of this activated carbon treated ligand solution were put into a dried 20 cc vial. Into this vial was also placed 0.497 grams of anhydrous $NiCl_2$ and 0.097 grams of finely divided zinc metal. A small magnetic stirring bar was added to the vial. The vial was capped and placed into a heated aluminum block that had been pre-heated to 100 deg C. A stop watch was started when the vial was placed into the heated block. The contents of the vial were agitated using a rotating magnetic bar coupled to the magnetic bar inside the vial. At 1.5 hours a sample was taken of the solution. Analysis of this sample showed 3100 ppm of Ni as catalyst in solution. This is about 7 times the amount of catalyst made in the Comparative Example.

Example 7

This example shows the benefit of treating crude ligand with a large pore zeolite.

5 cc of 13X molecular sieves, which had been previously activated by drying overnight at 350 deg C., was loaded into a 50 cc syringe body. 20 cc of 3-pentenenitrile was flushed through the resin and was disposed of. About 15 grams of "Ligand VII Stock Solution" was then allowed to drain through the sieves. The ligand solution was re-analyzed and found to have about 20 wt % ligand in it.

12.031 grams of this 13X molecular sieves treated ligand solution were put into a dried 20 cc vial. Into this vial was also placed 0.493 grams of anhydrous $NiCl_2$ and 0.091 grams of finely divided zinc metal. A small magnetic stirring bar was added to the vial. The vial was capped and placed into a heated aluminum block that had been pre-heated to 100 deg C. A stop watch was started when the vial was placed into the heated block. The contents of the vial were agitated using a rotating magnetic bar coupled to the magnetic bar inside the vial. At 1.5 hours a sample was taken of the solution. Analysis of this sample showed 2490 ppm of Ni as catalyst in solution. This is about 6 times the amount of catalyst made in the Comparative Example.

Example 8

This example shows the benefit of extracting crude ligand with methylglutaronitrile.

20 grams of "Ligand VII Stock Solution" was combined with 20 grams of methyl glutaronitrile in an air tight 100 milliliter microreactor. This microreactor was outfitted with an over head stirrer, a heating mantel, a distillation head, a dip tube to draw off material out of the flask and an addition funnel. This material was heated under vacuum to 60 to 80 deg C. to strip off the 3-pentenenitrile. This solution was allowed to cool and about 20 grams of cyclohexane was added to the flask. Two liquid phases formed. This solution was agitated and allowed to settle. The methylglutaronitrile formed a heavy liquid phase which was drawn off and discarded as waste. About 20 grams of 3-pentenenitrile was added to the flask. The flask was heated again under vacuum to about 45 deg C. and the cyclohexane was stripped off. The resulting solution was allowed to cool. A sample showed this final extracted ligand solution to have about 17 wt % ligand in it.

12.093 grams of this extracted ligand solution was put into a dried 20 cc vial. Into this vial was also placed 0.494 grams of anhydrous $NiCl_2$ and 0.095 grams of finely divided zinc metal. A small magnetic stirring bar was added to the vial. The vial was capped and placed into a heated aluminum block that had been pre-heated to 100 deg C. A stop watch was started when the vial was placed into the heated block. The contents of the vial were agitated using a rotating magnetic bar coupled to the magnetic bar inside the vial. At 1.5 hours a sample was taken of the solution. Analysis of this sample showed 3990 ppm of Ni as catalyst in solution. This is about 9 times the amount of catalyst made in the Comparative Example.

Example 9

This example shows the benefit of adding a Lewis acid such as $ZnCl_2$ to crude ligand.

12.059 grams of "Ligand VII Stock Solution" were put into a dried 20 cc vial. Into this vial was also placed 0.495 grams of anhydrous $NiCl_2$, 0.098 grams of finely divided zinc metal and 0.175 grams of anhydrous $ZnCl_2$. A small magnetic stirring bar was added to the vial. The vial was capped and placed into a heated aluminum block that had been pre-heated to 100 deg C. A stop watch was started when the vial was placed into the heated block. The contents of the vial were agitated using a rotating magnetic bar coupled to the magnetic bar inside the vial. At 1.5 hours a sample was taken of the solution. Analysis of this sample showed 5160 ppm of Ni as catalyst in solution. This is about 12 times the amount of catalyst made in the Comparative Example.

Example 10

This example shows the benefit of extracting crude ligand with ethylene glycol.

20 grams of "Ligand VII Stock Solution" was combined with 20 grams of ethylene glycol in an air tight 100 milliliter microreactor. This microreactor was outfitted with an over head stirrer, a heating mantel, a distillation head, a dip tube to draw off material out of the flask and an addition funnel. Two liquid phases formed. This solution was agitated and allowed to settle. The ethylene glycol formed a heavy liquid phase which was drawn off as waste. About 20 grams of 3-pentenenitrile was added to the flask. The flask was heated under vacuum to about 45 deg C., and the cyclohexane was stripped off. The resulting solution was allowed to cool. A sample showed this final extracted ligand solution to have about 18 wt % ligand in it.

12.015 grams of this ligand solution in 3-pentenenitrile was put into a dried 20 cc vial. Into this vial was also placed 0.516 grams of anhydrous NiCl$_2$ and 0.095 grams of finely divided zinc metal. A small magnetic stirring bar was added to the vial. The vial was capped and placed into a heated aluminum block that had been pre-heated to 100 deg C. A stop watch was started when the vial was placed into the heated block. The contents of the vial were agitated using a rotating magnetic bar coupled to the magnetic bar inside the vial. At 1.5 hours a sample was taken of the solution. Analysis of this sample showed 4870 ppm of Ni as catalyst in solution. This is about 11 times the amount of catalyst made in the Comparative Example.

What is claimed:

1. A process for preparing a nickel/ligand catalyst, said process comprising:

(a) contacting one molar equivalent of PCl$_3$ with about two molar equivalents of R$^1$OH, wherein R$^1$ is a substituted or unsubstituted aryl group, and at least two molar equivalents of an organic base at a temperature between about −25 deg C. and about 35 deg C., in a solvent to produce a first reaction product comprising a di(aryloxy) phosphorous chloride of the formula (R$^1$O)$_2$PCl and a salt formed from the organic base, said salt being substantially insoluble in the first reaction product;

(b) contacting the first reaction product at a temperature between about −25 deg C. and about 35 deg C. with about one half molar equivalent of HO—Z—OH, wherein Z is a substituted or unsubstituted aryl group different from R$^1$, to produce a second reaction product comprising a solids content, provided that if less than three molar equivalents of organic base are used in step (a), then sufficient organic base is used in step (b) to bring the total amount of organic base used in steps (a) and (b) combined to at least three molar equivalents of organic base relative to the PCl$_3$;

(c) separating the solids content from the second reaction product by filtration or extraction with water to produce a crude ligand mixture, said solids content comprising a salt formed from the organic base used in step (a) and optionally in step (b);

(d) contacting the crude ligand mixture with at least one member selected from the group consisting of (i) a weakly acidic organic resin, (ii) a weakly basic organic resin, (iii) a high-surface-area organic resin, (iv) activated carbon, (v) aluminosilicate zeolite, (vi) a two phase solvent system for liquid-liquid extraction and (vii) a Lewis acid;

(e) recovering from the product of step (d) a solution containing a ligand of the formula (R$^1$O)$_2$POZOP(OR$^1$)$_2$; and (f) contacting the solution of step (e) with nickel chloride in the presence of a nitrile solvent and a reducing metal which is more electropositive than nickel to produce the nickel/ligand catalyst.

2. The process of claim 1 wherein the reducing metal is selected from the group consisting of Na, Li, K, Mg, Ca, Ba, Sr, Ti, V, Fe, Co, Cu, Zn, Cd, Al, Ga, In, and Sn.

3. The process of claim 2 further comprising separating unreacted nickel chloride from the reaction product produced by step (f).

4. The process of claim 2 where the reducing metal is Zn or Fe.

5. The process of claim 4 wherein step (f) is conducted at a temperature between about 30 to 110 deg C. and at a pressure between about 5 to 50 psia (34 to 340 kPa).

6. The process of claim 5 wherein step (f) is conducted at a temperature between about 50 to 100 deg C.

7. The process of claim 6 wherein the molar ratio of nickel chloride to reducing metal is 0.1:1 to 50:1.

8. The process of claim 7 wherein the molar ratio of nickel chloride to reducing metal is 2:1 to 25:1.

9. The process of claim 8 wherein R$^1$ is phenyl, unsubstituted or substituted with one or more C$_1$ to C$_{12}$ alkyl or C$_1$ to C$_{12}$ alkoxy groups; or naphthyl, unsubstituted or substituted with one or more C$_1$ to C$_{12}$ alkyl or C$_1$ to C$_{12}$ alkoxy groups; and Z is independently selected from the group consisting of structural formulae II, III, IV, V, and VI:

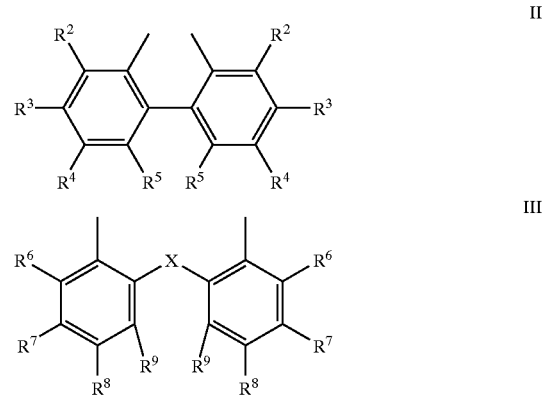

wherein

R$^2$, R$^3$, R$^4$, R$^5$, R$^6$, R$^7$, R$^8$, and R$^9$ are independently selected from the group consisting of H, C$_1$ to C$_{12}$ alkyl, and C$_1$ to C$_{12}$ alkoxy;

X is O, S, or CH(R$^{10}$);

R$^{10}$ is H or C$_1$ to C$_{12}$ alkyl;

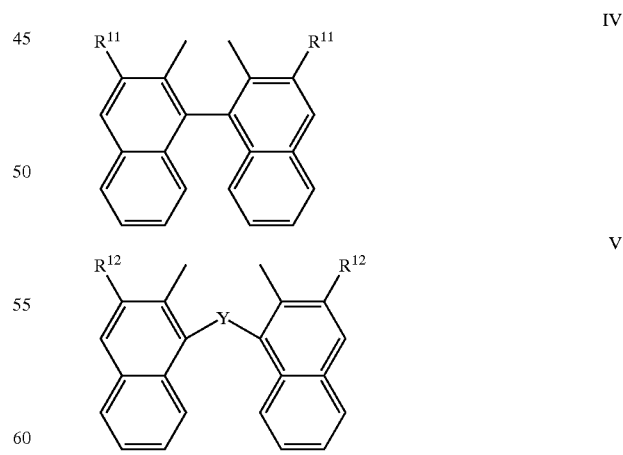

wherein

R$^{11}$ and R$^{12}$ are independently selected from the group consisting of H, C$_1$ to C$_{12}$ alkyl, C$_1$ to C$_{12}$ alkoxy, and CO$_2$R$^{13}$, R$^{13}$ is C$_1$ to C$_{12}$ alkyl or C$_6$ to C$_{10}$ aryl, unsubstituted or substituted, with C$_1$ to C$_4$ alkyl;

Y is O, S, or CH($R^{14}$);
$R^{14}$ is H or $C_1$ to $C_{12}$ alkyl;

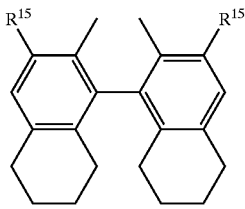

VI wherein
$R^{15}$ is selected from the group consisting of H, $C_1$ to $C_{12}$ alkyl, $C_1$ to $C_{12}$ alkoxy and $CO_2R^{16}$;
$R^{16}$ is $C_1$ to $C_{12}$ alkyl or $C_6$ to $C_{10}$ aryl, unsubstituted or substituted with $C_1$ to $C_4$ alkyl.

10. The process of claim 1 wherein liquid-liquid extraction is used in step 1(d), and one phase of the two-phase solvent system contains a solvent which is selected from the group consisting of adiponitrile, methylglutaronitrile and ethylene glycol, and the other phase is a solvent selected from the group consisting of cyclic or acyclic hydrocarbons containing 5 to 25 carbon atoms.

11. The process of claim 10 wherein one phase of the two-phase solvent system for liquid-liquid extraction in step 1(d) is cyclohexane.

12. The process of claim 1 wherein a Lewis acid is used in step 1(d) and is selected from the group consisting of $ZnCl_2$ and $FeCl_2$.

13. The process of claim 1 wherein a weakly acidic resin comprised of an organic polymer containing carboxylic acid functional groups is used in step 1(d).

14. The process of claim 1 wherein a weakly basic resin comprised of an organic polymer containing amine functional groups is used in step 1(d).

15. The process of claim 1 wherein a high surface area organic resin comprised of polystyrene or polyacrylate polymers is used in step 1(d).

16. The process of claim 1 wherein activated carbon is used in step 1(d).

17. The process of claim 1 wherein an aluminosilicate zeolite is used in step 1(d).

* * * * *